United States Patent [19]
Van Opdorp et al.

[11] Patent Number: 5,177,285
[45] Date of Patent: Jan. 5, 1993

[54] PROCESS FOR WET AROMATIC ALKYLATION AND DRY AROMATIC TRANSALKYLATION

[75] Inventors: Peter J. Van Opdorp, Naperville; Brian M. Wood, Glenview, both of Ill.

[73] Assignee: UOP, Des Plaines, Ill.

[21] Appl. No.: 812,154

[22] Filed: Dec. 23, 1991

[51] Int. Cl.⁵ .............................. C07C 2/66
[52] U.S. Cl. .................. 585/467; 585/301; 585/302; 585/323; 585/446
[58] Field of Search .............. 585/323, 467, 446

[56] References Cited

U.S. PATENT DOCUMENTS

| | | | |
|---|---|---|---|
| 4,051,091 | 9/1977 | Shibayama et al. | 260/29.2 TN |
| 4,083,886 | 4/1978 | Michalko | 260/672 T |
| 4,459,426 | 7/1984 | Inwood et al. | 585/475 |
| 4,587,370 | 5/1986 | De Graff | 585/450 |
| 4,695,665 | 9/1987 | De Graff | 585/450 |
| 4,761,513 | 3/1988 | Steacy | 585/467 |
| 4,870,222 | 9/1989 | Bakas et al. | 585/323 |
| 4,891,458 | 2/1990 | Innes et al. | 585/323 |
| 5,030,786 | 7/1991 | Shamshoum et al. | 585/467 |
| 5,073,653 | 12/1991 | Butler | 585/323 |
| 5,077,445 | 12/1991 | Le | 585/446 |
| 5,081,323 | 1/1992 | Innes et al. | 585/453 |

Primary Examiner—Anthony McFarlane
Attorney, Agent, or Firm—Thomas K. McBride; John G. Tolomei

[57] ABSTRACT

A process for the production of alkylaromatic hydrocarbons uses a high water content in an alkylation zone and a low water content in a transalkylation zone to improve yields improve process yields and catalyst life. An aromatic feed and an acyclic feed are first passed through the alkylation reaction zone that operates at a high water content. A separator receives the effluent from the alkylation reaction zone and removes water from a sidecut of unreacted aromatic feed. The sidecut of aromatic feed and a stream of polyalkylated aromatics are contacted in the transalkylation zone. The differing water content improves the operation of both the alkylation zone and the transalkylation zone.

18 Claims, 1 Drawing Sheet

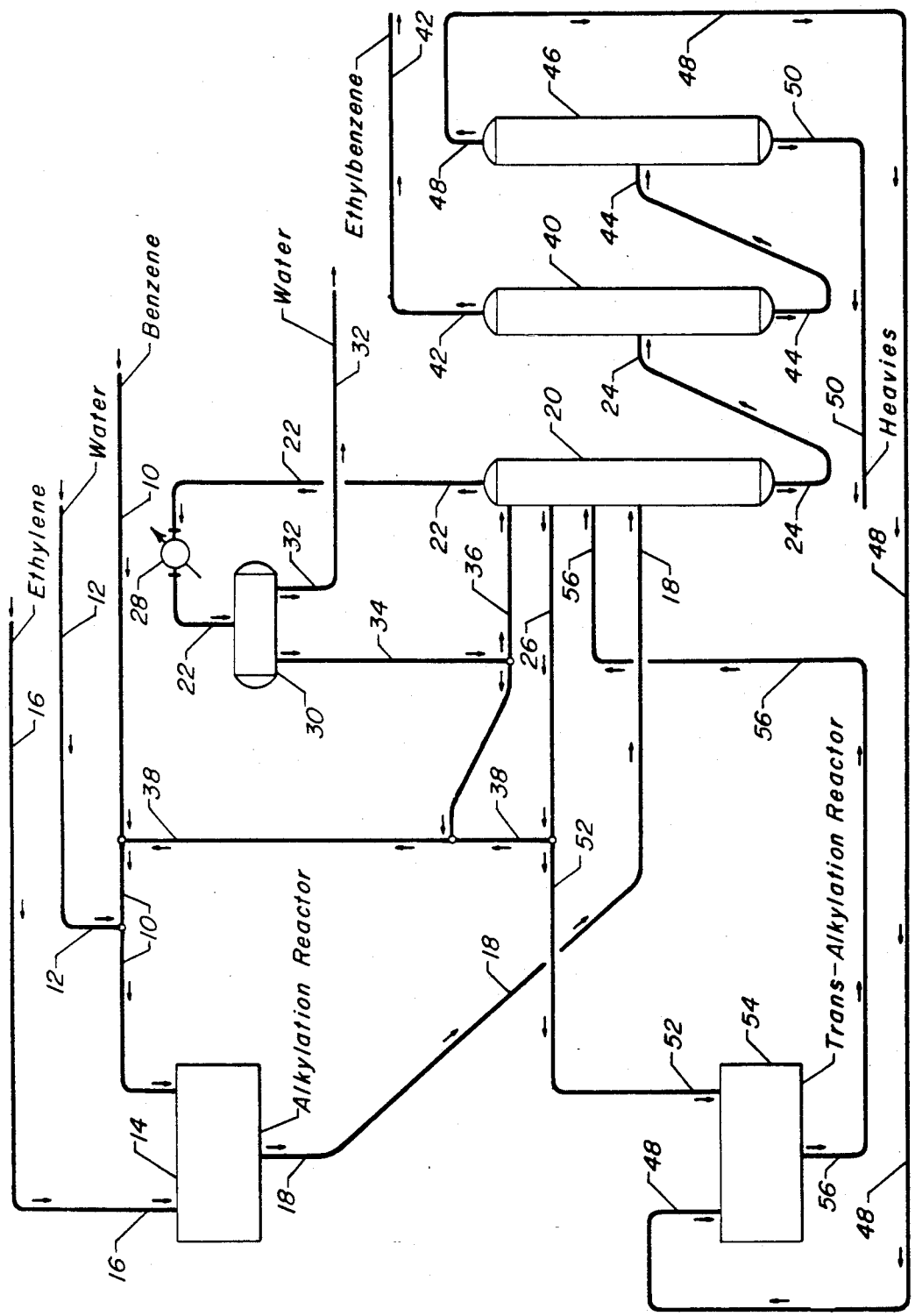

PROCESS FOR WET AROMATIC ALKYLATION AND DRY AROMATIC TRANSALKYLATION

FIELD OF THE INVENTION

The invention relates to a hydrocarbon conversion process. The invention more specifically relates to the production of alkylaromatic hydrocarbons by the reaction of an acyclic olefinic hydrocarbon with an aromatic feed hydrocarbon.

PRIOR ART

The alkylation of aromatic hydrocarbons such as benzene using solid catalysts is a well-developed art which is practiced commercially in large scale industrial units. One commercial application of this process is the alkylation of benzene with ethylene to produce ethyl benzene which is subsequently used to produce styrene. Another application is the alkylation of benzene with propylene to form cumene (isopropylbenzene), which is subsequently used in the production of phenol and acetone. Those skilled in the art are therefore familiar with the general design and operation of such alkylation process.

The prior art is well described in the literature. For instance, a typical flow scheme suitable for the commerical production of cumene is depicted in U.S. Pat. No. 4,051,191 issued to D. J. Ward. This reference describes in some detail, catalyst, reaction conditions, and separatory methods suitable for the recovery of cumene. The reactor effluent is passed into a rectification zone in which propane, charged to the process in admixture with the feed propylene, is separated for recycling and for rejection from the process. Liquid phase hydrocarbons recovered in the rectification zone are then passed into a two-column fractionation train comprising a recycle column and a cumene or product column. The benzene feed aromatic hydrocarbon is recycled from the top of the first fractionation column. The product cumene is recovered from the top of the second fractionation column, with heavy aromatic by-products being withdrawn from the bottom of the second column.

U.S. Pat. Nos. 4,695,665 and 4,578,370 issued to R. R. DeGraff are particularly directed to the separation of products and the recovery of recycle streams from processes for the alkylation of aromatic hydrocarbons and U.S. Pat. No. 4,695,665 discloses the use of a flash drum in combination with an effluent rectifier to recover unreacted feed components.

U.S. Pat. No. 4,083,886 describes a process for the transalkylation of the alkylaromatic hydrocarbons that uses a zeolitic catalyst.

U.S. Pat. No. 4,891,458 describes the use of beta zeolite for the alkylation of aromatic hydrocarbons with alkenes to produce polyalkylated aromatics.

U.S. Pat. No. 5,030,786 discloses an alkylation process wherein the feedstream is dehydrated to enhance the performance of beta or Y type zeolites in the alkylation process.

The performances of aromatic alkylation processes are influenced by the stability and activity of the catalysts in the operating environment of the process. Currently available catalysts for the alkylation of aromatic hydrocarbons typically provide a relatively low aromatics conversion. This stems in part from the need to maintain a high ratio of aromatic substrate to alkenes that improves the selectivity of the alkylation catalyst for the desired monoalkylated products. Nevertheless typical alkylation processes still produce a relatively large amount of polyalkylated aromatic products that are transalkylated by contact with a transalkylation catalyst and a additional aromatic substrate. Therefore, alkylation processes will typically have an alkylation zone and a transalkylation reaction zone. In order to improve alkylation processes, means are continually sought to improve the performance of the catalyst systems in both the alkylation and transalkylation zones.

BRIEF SUMMARY OF THE INVENTION

The principal object of this invention is to improve the performance of the alkylation zone and transalkylation zone in an aromatic alkylation process. This invention further focuses on the use of zeolitic catalyst and the discovery that significantly different moisture contents for the alkylation zone and the transalkylation zone will improve the performance of the zeolitic catalyst in the alkylation and transalkylation reactors.

This invention is the operation of an alkylation zone and a transalkylation zone with zeolitic catalysts and divergent moisture concentrations to improve the stability and yields of a process for producing monoalkylated aromatics. A relatively high water concentration improves the performance of a zeolitic catalyst in an alkylation reaction zone. Conversely, a relatively low water concentration extends the life of a zeolitic catalyst in a transalkylation reaction zone. The process of this invention is arranged such that an alkylation reaction zone initially alkylates the feed components to produce an effluent stream containing unreacted aromatics and polyalkyl aromatics. A separation zone arrangement facilitates the recovery of unreacted aromatics and the polyalkyl aromatics as a transalkylation zone recycle stream and maintains a low moisture content in a recycle stream. The low moisture content recycle stream supplies the primary feed to the transalkylation zone. The low moisture content of the recycle streams preserves the activity of the transalkylation catalyst. Thus, in one aspect of the invention the separation of the alkylation zone product stream conveniently reduces the water content of the unconverted aromatic hydrocarbon stream to a suitable level for use in the transalkylation zone. Lowering the moisture content of the transalkylation zone has the advantage of preserving the stability of the catalyst in the transalkylation zone. The invention also has the advantage of facilitating the use of differing water contents in the transalkylation zone and particularly in the alkylation zone where a higher water concentration can advantageously attenuate catalyst activity.

Accordingly in one embodiment this invention is a process for the production of alkylaromatic hydrocarbons which comprises contacting an aromatic feed hydrocarbon and an acyclic feed hydrocarbon in an alkylation reaction zone with an alkylation catalyst at alkylation conditions including a water concentration of at least 200 wppm to promote alkylation and recovering an alkylation reaction zone effluent comprising unconverted feed aromatic hydrocarbons, product aromatic hydrocarbons, and polyalkylated aromatic hydrocarbons. The alkylation reaction zone effluent and a transalkylation zone effluent are separated into an alkylate stream comprising the product hydrocarbons and the polyalkylated aromatic hydrocarbons, a first recycle stream comprising a first portion of the unconverted feed hydrocarbons and a second recycle stream comprising a second portion of the unconverted feed hydrocarbons. The alkylate stream is divided into a third recycle stream comprising polyalkylated hydrocarbons and a product stream comprising the product hydrocarbons. The water concentration of the second recycle stream is maintained at less than 200 wppm. An admixture of the second and third recycle streams is contacted with a zeolitic transalkylation catalyst in a transalkylation reaction zone at transalkylation conditions to provide the transalkylation zone effluent.

BRIEF DESCRIPTION OF THE DRAWING

The FIGURE schematically illustrates the major equipment used in performing the process of this invention. In the process benzene carried by a line 10 is admixed with water from a line 12 and enters an alkylation reactor 14 along with ethylene from a line 16. After contact with a zeolitic catalyst, a line 18 carries the effluent from the alkylation reactor to a separation column 20. Separation column 20 separates the alkylation reactor effluent into an overhead of benzene, light non-aromatics and water taken by a line 22; a bottoms stream of ethylbenzene, polyethylbenzene and heavier hydrocarbons taken by a line 24; and a sidecut stream removed from an upper portion of the column by a line 26. The overhead stream 22 is condensed in a cooler 28 and passed on to a separator drum 30 from which water is removed by a line 32 and a benzene recycle stream is extracted by a line 34. A portion of the benzene recycle stream is refluxed back to column 20 by a line 36 and the remainder of the benzene returns to the alkylation reactor by a line 38 and line 10. Line 38 carries a portion of the benzene from line 26 along with a portion of the benzene from line 34 into line 10. Line 24 passes the ethylbenzene product and heavier aromatics into a second separation column 40 from which an overhead stream of ethylbenzene product is taken by a line 42 and a bottom stream of dialkylbenzene and heavier aromatics is withdrawn by a line 44. The diethylbenzene and heavier aromatics enter another separation column 46 from which dialkylbenzenes and heavier polyalkylated benzenes are withdrawn by a line 48; any remaining heavier hydrocarbons are withdrawn from the bottom of column 46 through a line 50. Dialkylbenzenes and other polyalkylated benzenes are returned by line 48 to a transalkylation reactor along with the contents of line 26 which contains a portion of the benzene withdrawn as a sidecut. An effluent stream from transalkylation reactor 54 containing additional ethylbenzene product and unconverted reactants is returned to column 20 via a line 56.

DETAILED DESCRIPTION OF THE INVENTION

This invention is suitable for a wide variety of feedstocks. Suitable aromatic feed hydrocarbons for this invention include various aromatic substrates. Such substrates can be alkylated aromatic hydrocarbons such as alkyl substituted benzenes but are preferably unsubstituted benzenes. The acyclic feed hydrocarbon or alkylating agent that may be used in the alkylation reaction zone also encompasses a broad range of hydrocarbons. Suitable alkylating agents include monoolefins, diolefins, polyolefins, acetylenic hydrocarbons and other substituted hydrocarbons but are preferably $C_2$-$C_4$ hydrocarbons. In the most preferred form of this invention, the alkylation agent will comprise $C_2$-$C_4$ monoolefins.

A catalyst promotes the initial alkylation in the alkylation reaction zone. A wide variety of catalysts can be used in the alkylation reaction zone. Suitable catalysts for use in the reaction zone will comprise any catalyst that does not suffer deleterious effects from the presence of water. Preferably a substantial quantity of water will enhance the performance of the alkylation catalyst. A substantial quantity of water is meant to include a concentration in the reactants of at least 200 wppm. The preferred catalyst for use in this invention is a zeolitic catalyst. The catalyst of this invention will usually be used in combination with a refractory inorganic oxide binder. Preferred binders are alumina or silica. Preferred alkylation catalysts are a type Y zeolite having an alumina or silica binder or a beta zeolite having an alumina or silica binder. The zeolite will be present in an amount of at least 50 wt.% of the catalyst and more preferably in an amount of at least 70 wt.% of the catalyst.

The alkylation reaction zone can operate under a broad range of operating conditions. Temperatures usually range from 100° C. to 325° C. with the range of about 150°-275° C. being preferred. Pressures can also vary within a wide range of about 1 atmosphere to 130 atmospheres. Since liquid phase conditions are generally preferred within the reaction zone, the pressure should be sufficient to maintain the reactants in such phase and will typically fall in a range of from 10 to 50 atmospheres. Reactants generally pass through the alkylation zone at a mass flow rate sufficient to yield a liquid hourly space velocity from 0.5 to 50 hrs$^{-1}$ and especially from about 1 to 10 hrs$^{-1}$.

The alkylation zone is ordinarily operated to obtain an essentially complete conversion of the alkylating agent to monoalkylate and polyalkylate. To achieve this effect, additional aromatic substrate will usually be charged to the reaction zone. Thus, the feed mixtures are introduced into the reaction zone at a constant rate and a molecular ratio of about 1:1 to 20:1 aromatic substrate to alkylating agent with a ratio of about 2:1 to 10:1 being preferred. As a result, in addition to product there will usually be a substantial amount of unreacted aromatic substrate that is removed with the product stream from the alkylation reaction zone.

As mentioned the alkylation reaction zone will often provide a wide variety of undesired by-products. For example, in the alkylation of benzene with ethylene to produce ethylbenzene, the reaction zone can also produce di- and triethylbenzene in addition to other ethylene condensation products. The transalkylation arrangement of this invention dealkylates the polyalkylated products in the presence of additional substrate to yield additional alkylate products. Therefore, a number of separation stages are needed to separate aromatic products from the additional by-products.

A number of combinations of columns and separators can be used to recover the desired alkyl aromatic product and produce recycle streams of aromatic substrate and polyalkylated aromatics for transalkylation. A common separation arrangement will use a first column to separate the aromatic substrate from the remaining heavier components of the product effluent and one or more additional separation columns will fractionate the aromatic product from lighter or heavy by-product streams. Heavy components that are not suitable for transalkylation are usually rejected from the process. In the case of ethylbenzene production the alkylation reaction zone effluent will enter a benzene column from which benzene is withdrawn overhead while higher boiling reaction products are passed on to an ethylbenzene column from which ethylbenzene product is withdrawn as an overhead. The higher boiling products from the ethylbenzene column enter a column which fractionates the polyalkylated benzene into an overhead stream for use as feed to the transalkylation reactor and provides a bottoms stream of heavier hydrocarbons that are rejected from the process.

Common arrangements for the recovery of aromatic substrate recovers benzene as the overhead from a fractionation column. An overhead condenser allows separation of water from the overhead stream and a portion of the aromatic hydrocarbon condensate returns to the column as reflux while the remainder is split between the alkylation reactor and transalkylation reactor. Traditionally, the overhead condenser was operated to reduce the water concentration to a level of about 550 wt. ppm. Although such water concentrations were acceptable and in many cases beneficial to the alkylation reactor operation, the same water concentrations have been found to deleteriously effect zeolitic catalyst in the transalkylation reactor. Therefore, many separation arrangements required further drying of that portion of the aromatic substrate that is returned from the overhead condenser to a transalkylation reactor.

This invention, in one aspect, provides a modification to such a separation arrangement that supplies an aromatic substrate having a low water concentration. In this arrangement, the aromatic substrate is withdrawn as a sidecut from an upper portion of the column. By the addition of a few extra trays to the distillation column, enough water removal can be achieved to reduce the concentration in the sidecut to less than 200 wt. ppm. Therefore, in accordance with this aspect of the invention, the separation column will be operated to withdraw an overhead that is condensed and passed to the alkylation reactor while a drier aromatic substrate stream is withdrawn from a slightly expanded upper section of the column and passed to the transalkylation reactor. Again, in the context of ethylbenzene separation, the modification of a benzene column to accomplish the required degree of sidecut drying will require the addition of about 3 trays. The volume of low moisture content aromatic substrate withdrawn from the column will usually be in excess of that required for the operation of the transalkylation reactor and the flow will be balanced by diverting the remainder into the alkylation reactor. The presence of additional dried aromatic substrate in the feed to the alkylation reactor can be suitably offset by water addition to the feed to the alkylation reactor.

As stated the alkylation reaction zone produces polyalkylated aromatic compounds as well as the desired monoalkylated aromatic product. These polyalkylated aromatics contact additional aromatic substrate in a transalkylation reactor to produce additional monoalkylated product. The transalkylation reaction zone of this invention will use a zeolitic catalyst. The zeolite will be present in an amount of at least 50 wt. % of the catalyst and more preferably in an amount of at least 90 wt. % of the catalyst. In most cases the zeolitic catalyst again includes an inorganic oxide binder. The preferred inorganic oxide for use in the transalkylation catalyst is alumina with gamma-alumina, eta-aluminum and mixtures thereof being particularly preferred. The zeolite may be present in a range of from 5 to 99 wt. % of the catalyst and the refractory inorganic oxide may be present in a range of from 5 to 95 wt. %. Preferred transalkylation catalysts are a type Y zeolite having an alumina or silica binder or a beta zeolite having an alumina or silica binder.

Again water has been found to have a deleterious effect on the zeolitic catalyst and prolonged contact with high concentrations of water will cause the catalyst to lose activity. In order to sustain adequate conversion from the transalkylation zone over a normal run period, the loss in activity is compensated by increasing severity of operation within the reaction zone. The increase in severity causes the transalkylation reactor to lose selectivity and ultimately results in a shortened length of run for the catalyst, a loss in product yields, or combination of the two. By operating the transalkylation reaction zone at a much lower water concentration than alkylation reaction zone, typically a water concentration of less than 200 wppm, no appreciable loss of activity is seen over a reasonable length of run for the process. The water concentration in the transalkylation reaction zone can be kept at very low levels. However, maintaining very low water concentrations in the transalkylation zone, i.e. less than 75 wppm, requires expensive dehydrating equipment and unnecessarily raises the expense of the transalkylation zone. Preferably, the water concentration in the transalkylation reaction zone will be greater than 100 wppm.

There is no requirement that the alkylation reaction zone and the transalkylation reaction zone use the same catalyst. This process is useful for any arrangement of alkylation reaction zone and transalkylation reaction zone wherein the operation of the former is benefited by a high water concentration and a high water concentration in the latter is detrimental. However, it has been found that the preferred catalyst for this invention, a high Y type zeolite contents in an alumina binder will perform very well when used in both the alkylation reaction zone and the transalkylation reaction zone. Therefore, in the preferred embodiment of this invention, both reaction zones will use the same catalyst.

The transalkylation reaction can be carried out in a broad range of operating conditions that include a temperature of from 100°–390° C. and pressure ranging from 1 to about 130 atmospheres. Again, the pressure would generally be selected so that the reactants will remain in the liquid phase. Accordingly, preferred pressures for the transalkylation reaction zone range from 10 to about 50 atmospheres. A liquid hourly space velocity of from 0.5 to 50 hrs$^{-1}$ is desirable for the transalkylation reaction zone with LHSV of from 0.5 to 5 hrs$^{-1}$ being preferred.

The beneficial operation of this invention will be further described in the context of an exemplified preferred embodiment which is the alkylation of ethylene with benzene to obtain ethylbenzene. The description of this invention in terms where preferred embodiment is not meant to limit the claims of this invention to the particular details disclosed herein. Both of these examples presented herein are based on engineering calculations and actual operating experience with similar processes.

EXAMPLE I

The flowscheme for this example is that shown in the FIGURE. In describing this example, valves, pumps, feeders, instruments and heat exchangers other than those necessary for an understanding and appreciation of the invention have been omitted. This example shows the performance of an ethylbenzene process arranged in accordance with this invention after at the end of a process run after approximately 500 days operation.

In this example benzene and ethylene feeds having purities of over 99.5 enter the process at a weight ratio of benzene to ethylene of about 6 to 1. Water is injected into the reactants entering the alkylation reactor to produce a water concentration of 500 wt. ppm. The reactants contact a Y zeolite catalyst in the alkylation reactor at a pressure of 39 atmospheres, a temperature in a range of from 240° to 265° C. and a liquid hourly space velocity of 5.0 hrs$^{-1}$.

A liquid effluent from the alkylation reactor along with a liquid transalkylation effluent enters a benzene column. 100 mass units of an overhead stream comprising benzene and water is taken overhead by line 20 and condenses in condensor 30 to produce a benzene stream having a water concentration of about 540 wppm of which 62.8 mass units are refluxed to the benzene column and the remainder is admixed with the feed to the alkylation reaction zone. Another benzene stream having a water concentration of about 75 wppm is withdrawn as the sidecut 36 which transfers approximately 22.6 mass units to the transalkylation reaction zone by a line 52. Another 11.4 mass units withdrawn from the bottom of the benzene column by line 24 and separated in an ethylbenzene column which withdraws ethylbenzene product and passes the remainder on to a polyethylbenzene column from which 1.6 mass units of polyalkylated benzene is withdrawn and returned to the transalkylation reactor via line 54, into which sufficient water is added to raise the water concentration to 120 wppm.

The transalkylation reaction zone contacts the combined feed with the same catalyst as in the alkylation reaction zone at a LHSV of 2.3 hrs$^{-1}$, a pressure of 39 atmospheres and an initial temperature of 210° C. The transalkylation zone operates for a total of 500 days. In order to maintain constant conversion in the transalkylation zone the temperature of the transalkylation zone is gradually increased and reaches a temperature of 270° C. by the end of the 500 day run.

EXAMPLE II

This example demonstrates the operation of a alkylation and transalkylation zones in process for the alkylation of benzene with ethylene that does not use the method of this invention to dry the recycle benzene to the transalkylation zone. Essentially the same process with the same feeds is carried out in this example with the exception that no sidecut is withdrawn from the benzene column. All of the recycle benzene for both the transalkylation reactor and the alkylation reactor are recovered overhead from the benzene column. A total of about 123 mass units are recovered in the overhead stream and pass through the condensing portion of the column to produce a recycle stream having a water concentration of 540 wppm. About 62.8 mass units of the overhead stream are refluxed to the benzene column. Of the remaining recycle, about 37.2 mass units enter the alkylation reactor and about 22.6 mass units pass on to the transalkylation reactor. The alkylation reaction zone and the transalkylation zone use the same catalyst and operate in a similar manner to the alkylation and transalkylation zone in Example I to produce essentially the same products. The transalkylation zone again initially operates at a temperature of 210° C. In order to maintain constant conversion, the temperature of the transalkylation zone increases to 270° C. after 286 days.

As a result it can be seen that the deactivation in the transalkylation zone that uses the water removal method of this invention experiences a significantly reduced deactivation rate.

What is claimed is:

1. A process for the production of alkylaromatic hydrocarbons which comprises:
   a) contacting an aromatic feed hydrocarbon and an acyclic feed hydrocarbon in an alkylation reaction zone with an alkylation catalyst at alkylation conditions including a water concentration of at least 200 wppm to promote alkylation and recovering an alkylation reaction zone effluent comprising unconverted feed aromatic hydrocarbons, product aromatic hydrocarbons, and polyalkylated aromatic hydrocarbons;
   b) passing said alkylation reaction zone effluent and a transalkylation zone effluent to separation column, separting said alkylation reaction zone effluent and said transalkylation zone effluent, withdrawing an alkylate stream comprising said product hydrocarbons and said polyalkylated aromatic hydrocarbons as a bottoms stream for said column, withdrawing a first recycle stream comprising a first portion of said unconverted feed aromatic hydrocarbons and water as an overhead stream from said column, and withdrawing a second recycle stream comprising a second portion of said unconverted feed aromatic hydrocarbons and having a water concentration of less than 200 wppm as a sidecut from said column;
   c) separating said alkylate stream into a third recycle stream comprising said polyalkylated hydrocarbons and a product stream comprising said product hydrocarbons; and,
   (d) admixing said second and third recycle streams and contacting said second and third recycle streams with a zeolite transalkylation catalyst in a transalkylation reaction zone at transalkylation conditions that include a water concentration of less than 200 wppm, to provide said transalkylation zone effluent.

2. The process of claim 1 wherein said aromatic feed hydrocarbon comprises benzene and said acyclic feed hydrocarbon comprises ethylene.

3. The process of claim 1 wherein said alkylation and transalkylation catalysts comprise a zeolite and alumina.

4. The process of claim 3 wherein said catalysts comprise alumina and at least 50 wt. % Y-zeolite.

5. The process of claim 1 wherein said first and second alkylation catalysts have the same composition.

6. The process of claim 1 wherein said alkylation reaction zone operates under liquid phase conditions at a temperature in a range of from 100° to 325° C. and a pressure of from 10 to 50 atm.

7. The process of claim 1 wherein said transalkylation reaction zone operates at a temperature in a range of from 100° to 390° C. and a pressure of from 10 to 50 atm.

8. The process of claim 1 wherein said water concentration in said transalkylation reaction zone is greater than 100 wppm.

9. The process of claim 1 wherein said first recycle stream is passed to said alkylation reaction zone.

10. The process of claim 1 wherein said second recycle stream has a water concentration of at least 100 wppm.

11. A process for the production of ethylbenzene that comprises:
   a) contacting a benzene feed and an ethylene feed in an alkylation reaction zone with an alkylation catalyst at alkylation conditions including a water concentration of at least 200 wppm to promote alkylation and recovering an alkylation reaction zone effluent comprising benzene, ethylbenzene, diethylbenzene and heavier aromatic hydrocarbons;
   b) passing said alkylation reaction zone effluent and a transalkylation reaction zone effluent to a separation column, withdrawing an alkylate stream comprising ethylbenzene, diethylbenzene, and heavier aromatic hydrocarbons from the bottom of said column, a first recycle stream comprising benzene as an overhead from said column, and a second recycle stream comprising benzene as a sidecut stream from said column said second recycle stream having a water concentration of less than 200 wppm water;
   c) separating said alkylate stream into an intermediate separation stream comprising said diethylbenzene and heavier hydrocarbons and a product stream comprising said ethylbenzene;
   d) separating said intermediate separation stream into a third recycle stream comprising said diethylbenzene and a heavy aromatic stream comprising said heavier hydrocarbons; and,
   e) admixing said second and third recycle streams and contacting said admixed first and second recycle streams with a transalkylation catalyst in a transalkylation reaction zone at transalkylation conditions that include a water concentration of less than 200 wppm to provide said transalkylation zone effluent.

12. The process of claim 11 wherein said alkylation and transalkylation catalyst comprises alumina and at least 50 wt. % Y zeolite.

13. The process of claim 12 wherein said alkylation and transalkylation catalysts have the same composition.

14. The process of claim 13 wherein said alkylation reaction zone operates under liquid phase conditions at a temperature in a range of from 100° to 325° C. and a pressure of from 10 to 50 atm.

15. The process of claim 14 wherein said transalkylation reaction zone operates at a temperature in a range of from 100° to 390° C. and a pressure of from 10 to 50 atm.

16. The process of claim 15 wherein said water concentration in said transalkylation zone is greater than 100 wppm.

17. The process of claim 16 wherein water is condensed from said first recycle stream and a portion of said first recycle stream having a lowered water content is refluxed to said separation column.

18. The process of claim 11 wherein at least a portion of said first recycle stream is returned to said alkylation reaction zone.

* * * * *